United States Patent [19]

Carter et al.

[11] Patent Number: 5,019,373

[45] Date of Patent: May 28, 1991

[54] ORAL COMPOSITION

[75] Inventors: Peter Carter, Burton; Kevin Hammond, Wirral, both of Great Britain

[73] Assignee: Chesebrough-Pond's USA Co., Division of Conopco, Inc., Greenwich, Conn.

[21] Appl. No.: 442,741

[22] Filed: Nov. 29, 1989

[30] Foreign Application Priority Data

Dec. 1, 1988 [GB] United Kingdom ............... 8828018

[51] Int. Cl.$^5$ .................... A61K 7/16; A61K 7/18
[52] U.S. Cl. ............................ 424/52; 424/49; 424/57
[58] Field of Search ................... 424/49, 52, 57

[56] References Cited

U.S. PATENT DOCUMENTS

| | | | |
|---|---|---|---|
| 2,758,093 | 8/1956 | Ernst et al. | |
| 4,036,950 | 7/1977 | Baines et al. | 424/57 |
| 4,123,517 | 10/1978 | Baines et al. | 424/57 |
| 4,139,485 | 2/1979 | Imokawa et al. | 252/135 |
| 4,152,421 | 5/1979 | Tsutsumi et al. | 424/57 |
| 4,238,476 | 12/1980 | Harvey | 424/57 |
| 4,264,580 | 4/1981 | Barberio | 424/57 |
| 4,301,143 | 11/1981 | Barberio | 424/57 |
| 4,350,680 | 9/1982 | Harvey et al. | 424/57 |
| 4,459,283 | 7/1984 | Harvey et al. | 424/57 |
| 4,526,710 | 7/1985 | Fujisawa et al. | 252/545 |
| 4,686,211 | 8/1987 | Hara et al. | 514/148 |
| 4,707,292 | 11/1987 | Sano et al. | 252/174.16 |
| 4,832,946 | 5/1989 | Green | 424/70 |
| 4,871,396 | 10/1989 | Svjitia et al. | 106/286.8 |

FOREIGN PATENT DOCUMENTS

| | | | |
|---|---|---|---|
| 0224796 | 11/1986 | European Pat. Off. | |
| 0224796 | 6/1987 | European Pat. Off. | |
| 2744980 | 4/1978 | Fed. Rep. of Germany | |
| 8901023 | 2/1989 | PCT Int'l Appl. | |
| 2084015 | 4/1982 | United Kingdom | 424/57 |
| 2084463 | 4/1982 | United Kingdom | 424/57 |

OTHER PUBLICATIONS

European Search Report and Annex.
Meguru et al., C.A. 79: 149325x (1973).
Tsutsumi et al., C.A. 89: 117572q (1978).
Yaguchi et al., C.A. 109: 57112m (1988).

*Primary Examiner*—Shep K. Rose
*Attorney, Agent, or Firm*—Milton L. Honig

[57] ABSTRACT

The present invention relates to oral compositions such as dentifrices or mouthwashes.

By inclusion therein of a shorter chain mono- and dialkylphosphate as surfactant, a mild product is obtained which also has improved anti-caries properties.

Preferred are sodium mono- and di-octyl phosphates for use in these compositions.

4 Claims, No Drawings

ORAL COMPOSITION

BACKGROUND OF THE INVENTION

The invention relates to aqueous compositions suitable for use in oral hygiene, especially for cleaning the mouth and the teeth. In particular, the invention is concerned with highly improved detergent compositions suitable for use as dentifrices and mouth washes.

The damaging effect of conventional detergents used to cleanse the mucosae, particularly the mouth, has been the subject of intense study for many years in a search for mild products, which not only cleanse efficiently, but also leave the mouth and teeth with a pleasant after feel, without irritation or other chemical damage to the gums or mucosae.

We have now discovered quite unexpectedly, that by selection of a specific dialkyl phosphate in the form of a salt, together with a monoalkyl phosphate salt to modify the foam characteristics of the product, a composition can be obtained which in use is capable of producing superior foam characteristics and cleaning power, that cannot be matched by any other product. Furthermore, the composition is so mild that it can safely be used for cleansing the teeth and mucosae, including the gums when diseased or damaged. It is particularly useful for cleaning sensitive gums, for example when gingivitis is present, and also possesses improved anti-caries properties. Also, following use of the composition in the mouth, the taste of foods and drinks subsequently consumed is not changed, in contrast to the bitter after-taste that can result when more conventional surfactants are employed.

DEFINITION OF THE INVENTION

Accordingly, the invention provides an aqueous composition suitable for use as a dentifrice and mouthwash which comprises:

(a) a monoalkyl or monoalkenyl phosphate salt (or mixtures thereof) having the structure:

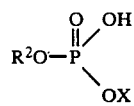

(b) a dialkyl or dialkenyl phosphate salt (or mixtures thereof) having the structure:

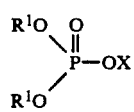

and optionally:

(c) a dialkyl or dialkenyl phosphate salt having the structure:

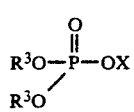

where $R^1$ is the same or different and is chosen from saturated or unsaturated, branched or unbranched alkyl or alkenyl groups having an average of from 6 to 9 carbon atoms, and $R^2$ is chosen from alkyl or alkenyl groups having an average of from 6 to 18 carbon atoms, $R^3$ is chosen from alkyl or alkenyl groups having an average of from 10 to 18 carbon atoms, and X is chosen from sodium, potassium, ammonium, substituted ammonium and alkylolamine.

DISCLOSURE OF THE INVENTION

The Mono-Alkyl or Monoalkenyl Phosphate Salt

The composition according the invention comprises a monoalkyl or monoalkenyl phosphate salt (or mixtures thereof) which is intended to modify the foam characteristics and the after-use feel of the composition in the mouth. The monoalkyl or monoalkenyl phosphate salt has the structure:

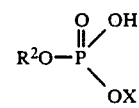

where $R^2$ is chosen from alkyl or alkenyl groups having an average of from 6 to 18 carbon atoms, and X is chosen from sodium, potassium, ammonium, substituted ammonium and alkanolamine.

The preferred monoalkyl phosphate salts are sodium monolauryl phosphate, triethanolamine monolauryl phosphate, and sodium monooctyl phosphate.

The amount of monoalkyl or monoalkenyl phosphate salt present in the composition of the invention is from 0.1, conveniently from 1 to 95%, preferably from 2 to 90% by weight.

The Shorter Chain Dialkyl or Dialkenyl Phosphate Salt

The composition according to the invention also comprises a dialkyl or dialkenyl phosphate salt (or mixtures thereof) having the structure:

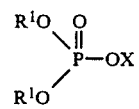

where $R^1$ is the same or different and is chosen from saturated or unsaturated, branched or unbranched alkyl or alkenyl groups having an average of from 6 to 9 carbon atoms, and X is chosen from sodium, potassium, ammonium, substituted ammonium and alkylolamine.

The preferred shorter chain dialkyl phosphate is doictyl phosphate and the preferred salts are sodium and alkylolamine salts, particularly the triethanolamine salt.

The amount of the shorter chain dialkyl or dialkenyl phosphate salt present in the composition of the invention is from 0.1, conveniently from 1 to 95%, preferably from 5 to 90% by weight.

The Longer Chain Dialkyl or Dialkenyl Phosphate Salt

The composition according to the invention can also optionally comprise a dialkyl or dialkenyl phosphate salt (or mixtures thereof) having the structure:

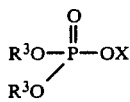

where
R[3] is chosen from alkyl or alkenyl groups having an average of from 10 to 18 carbon atoms, and
C is chosen from sodium, potassium, ammonium substituted ammonium and alkanolamine.

The preferred longer chain dialkyl phosphate salts, when present, are sodium dimyristyl phosphate and triethanolamine lauryl phosphate.

The amount of the longer chain dialkyl or dialkenyl phosphate salt, when present, is up to 50%, usually from 0.1 to 50%, preferably from 1 to 20% by weight of the composition.

The weight ratio of the monoalkyl or monoalkenyl phosphate salt to the longer chain dialkyl phosphate or dialkenyl salt is from 100:0 to 50:50, preferably 99:1 to 75:25.

Dentrifice and/of Mouthwash adjuncts

The composition according to the invention will also comprise adjuncts, that is other ingredients, conventionally employed in dentrifice and mouthwash formulations.

Examples of these adjuncts include:

Polishing agents (or abrasive agents), such as silicas, calcium hydrogenphosphate, calcium carbonate, calcium pyrophosphate, calcium hydroxyapatite and alumina;

Binders such as sodium carboxymethylcellulose, hydroxyethylcellulose, carrageenan, sodium alginate, gum arabic, xanthan gum, montmorillonite and hectorite;

Humectants, such as glycerin and, sorbitol; Therapeutic agents, such as organic antimicrobial agents; metal ions, including zinc, copper, tin and strontium, fluoride sources, such as sodium monofluorophosphate, sodium fluoride, stannous fluoride and amine fluorides; agents promoting the delivery of therapeutic agents such as polyvinylmethylether-maleic anhydride copolymers.

Antitartar agents, such as sodium and potassium pyrophosphate; anti-microbial agents such as 2,4,4' trichloro-2'-hydroxy-diphenylether (Triclosan);

Other surfactants, such as sodium lauryl sulphate and dodecylbenzene sulphonate;

Sweetening agents, such as soluble saccharin and Candarel; and flavouring agents such as oil of wintergreen, peppermint oil, spearmint oil and menthol.

The amount of dentrifice and/or mouthwash adjuncts to be incorporated in compositions according to the invention will be those conventionally employed in these products. By way of example, it can be stated that a dentrifice can contain the following ingredients in the amounts stated:

|  | % by weight |
| --- | --- |
| Polishing agent | 5 to 70 |
| Binder | 0.3 to 5 |
| Humectant | 5 to 60 |
| Medical agent | 0.001 to 2 |
| Sweetening agent and flavour | as desired |

| | % by weight |
| --- | --- |
| Water | balance |

In the above example, the amount of monoalkyl phosphate salt and dialkyl phosphate salt, as herein defined, can conveniently be from 0.2 to 5% by weight of the composition. The preferred mixture of monoalkyl and dialkylphosphates is a mixture of mono octyl and dioctylphosphate.

Water

The composition according to the invention also comprises an amount of water to act as a vehicle for the phosphate salts and other ingredients, to enable them to be provided at a concentration suitable for use as a dentifrice or mouthwash.

The amount of water present in the composition of the invention is accordingly from 10 to 99%, preferably from 15 to 90% by weight of the composition.

Co-surfactant

The composition according to the invention can also optionally comprise a co-surfactant, further to modify the surfactant properties of the dialkyl or dialkenyl salt.

Examples of co-surfactants include anionic surfactants other than the phosphate salts defined herein, as well as nonionic, amphoteric and zwitterionic surfactants.

Particularly preferred examples of amphoteric surfactants include amidoamine surfactants having the structure:

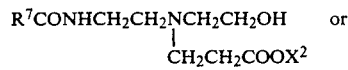

where
R[7] is chosen from saturated or unsaturated alkyl groups having an average of from 7 to 19 carbon atoms; and
X[2] is chosen from hydrogen, sodium, potassium, ammonium, substituted ammonium and alkanolamine.

Specific examples of amidoamine surfactants include those in which R[7] is represented by lauryl or myristyl and X[2] is represented by sodium or triethanolamine.

Particularly preferred examples of zwitterionic surfactants include hydroxysulphobetaines having the structure:

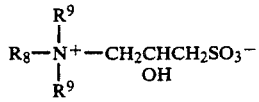

where
R[8] is chosen from saturated or unsaturated alkyl groups having from 8 to 18 carbon atoms; and
R[9] is the same or different and is chosen from alkyl groups having 1 or 2 carbon atoms.

Specific examples of hydroxysulphobetaines include:
lauryldimethyl hydroxysulphobetaine, and
lauryldiethyl hydroxysulphobetaine.

The amount of co-surfactant when present in the compositions according to the invention is usually up to 50%, preferably from 1 to 40% by weight.

PRODUCT FORM OF THE COMPOSITION

The composition according to the invention can take the form of a liquid, gel, paste or cream, intended to be dispensed from a capped container such as a bottle, tube, or a pump-operated dispenser.

EXAMPLES

The invention is further illustrated by reference to the following example.

EXAMPLE 1

This example illustrates a dentifrice.
The dentifrice contained the following ingredients:

| Ingredients | % w/w |
|---|---|
| Sodium dioctyl phosphate | 2 |
| Sodium monolauryl phosphate | 1 |
| Sodium dilauryl phosphate | 0.1 |
| carrageenan | 1.5 |
| sorbitol | 50 |
| sodium saccharin | 0.1 |
| silica | 20 |
| flavour | 0.1 |
| water | to 100 |

EXAMPLE 2

This Example illustrates further dentifrice formulations according to the invention

| Ingredients | % by weight |
|---|---|
| Abrasive silica | 10.0 |
| Thickening silica | 8.5 |
| Sodium carboxymethylcellulose | 0.9 |
| polyethyleneglycol 1500 | 5.0 |
| sorbitol (70%) | 45.0 |
| sodium monofluorophosphate | 0.82 |
| zinc citrate | 0.5 |
| saccharine | 0.2 |
| titanium dioxide | 1.0 |
| flavour | 1.0 |
| surfactant | * |
| water to 100 | |

*the surfactant can be
(1) 0.5% sodium laurylsulphate + 1.85% sodium dioctylphosphate + 0.15% disodium mono octylphosphate or
(2) 2.316% sodium dioctylphosphate + 0.184% disodium mono octylphosphate or
(3) 4.362% sodium dioctylphosphate + 0.368% disodium mono octylphosphate.

* the surfactant can be 1) 0.5% sodium laurylsulphate +1.85% sodium dioctylphate +0.15% disodium mono octylphosphate or 2) 2.316% sodium dioctylphosphate +0.184% disodium mono octylphosphate or 3) 4.362% sodium dioctylphosphate +0.368% disodium mono octylphosphate.

EXAMPLE 3

An experiment was carried out in which the effect of a 1% DOP solution (containing 0.91% sodium dioctylphosphate and 0.072% disodium mono octylphosphate) was evaluated as a potential anticaries agent by its ability to reduce the demineralisation of dental enamel in-vitro. The method of Page was used (J. Dent. Res. 68 (1989) 587) and four treatments were tested, Placebo (water), 1% SLS (=sodium lauryl sulphate), 1% DOP and a 1 ppm Fluoride Solution (as Sodium Fluoride), a known anticaries agent (positive control). The results are shown in the table below for a study on six teeth:

| Treatment | Mean Calcium Demineralisation (ug cm$^{-2-1}$) | % Reduction Demin | Duncan Crogie at = 0.01 |
|---|---|---|---|
| Water | 1.52 (0.13)** | — | A |
| 1% SLS | 1.36 (0.11) | 10.5 (4.5) | A |
| 1% DOP | 0.89 (0.09) | 41.4 (6.0) | C |
| 1 ppm Fluoride | 1.25 (0.13) | 17.8 (4.8) | B |

**Figures in brackets are standard deviations.
+ Treatments with same letters not significantly different at a = 0.01 level.

The mean Calcium Demineralisation Rates and % Reduction in Demineralisation are calculated using the following formulae.

Calcium Demineralisation Rate =

$$\frac{\text{Calcium in Solution}}{(\text{Timein Acid}) \times (\text{Area of Exposed Enamel})}$$

% Reduction in Demineralisation =

$$\left[ 1 - \frac{\text{CDR (TEST)}}{\text{CDR (PLACEBO)}} \right] \times 100\%$$

The SLS treatment numerically showed a difference to the placebo (water) treatment but this was not satistically significant at the α=0.01 level (Duncan's Multiple Range Test). Both the fluoride (positive control) and the DOP treatment reduced the rate of enamel demineralisation significantly (α=0.01 level) in the test with the DOP treatment showing the greatest effect. The DOP treatment was satistically significantly better than the fluoride treatment in this test.

This experiment shows that DOP has potential anticaries activities, as it is able to protect dental enamel from demineralisation when exposed to acidic solutions.

EXAMPLE 4

In a panel test in which the effect of surfactants in mouthwashes on the perception of orange juice was assessed, no difference was found between 1% SLS or 1% DOP, on bitterness, sharpness and freshness, but the following improvements of DOP over SLS were perceived:

| orange taste | + 31% |
|---|---|
| sweetness | + 41% |
| drying | + 59% |
| smooth teeth | + 37% |

We claim:
1. An aqueous oral composition having an anticaries effect upon teeth which contains an essential anticaries agent which essentially comprises:
(a) from 0.1 to 95% by weight of a monoalkyl or monoalkenyl phosphate salt or mixtures thereof having the structure:

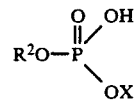

and (b) from 0.1 to 95% by weight of a dialkyl or dialkenyl phosphate salt or mixtures thereof having the structure:

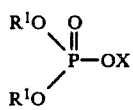

where
$R^1$ is the same or different and is chosen from saturated or unsaturated, branched or unbranched alkyl or alkenyl groups having an average of from 6 to 9 carbon atoms,
$R^2$ is chosen from alkyl or alkenyl groups having an average of from 6 to 18 carbon atoms and
X is chosen from sodium, potassium, ammonium, substituted ammonium and alkylolamine.

2. A composition according to claim 1, wherein $R^1$ and $R^2$ are octyl.

3. A composition according to claim 1, further comprising from 0.1 to 50% by weight of a dialkyl or dialkenyl phosphate salt having the structure:

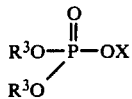

where $R^3$ is chosen from alkyl or alkenyl groups having an average of from 10 to 18 carbon atoms.

4. A composition according to claim 1, further comprising an effective amount of a therapeutic agent selected from the group consisting of sodium monofluorophosphate, sodium fluoride and stannous fluoride.

* * * * *